United States Patent
Dimke et al.

(12)

(10) Patent No.: US 6,677,468 B1
(45) Date of Patent: Jan. 13, 2004

(54) METHODS OF REDUCING CHLORIDE CONTENT IN EPOXY COMPOUNDS

(75) Inventors: Mark T. Dimke, Olean, NY (US); Richard E. Miller, Liberty Lake, WA (US)

(73) Assignee: Loctite Corporation, Rocky Hill, CT (US)

( * ) Notice: Subject to any disclaimer, the term of this patent is extended or adjusted under 35 U.S.C. 154(b) by 132 days.

(21) Appl. No.: 09/912,453

(22) Filed: Jul. 24, 2001

(51) Int. Cl.[7] ................ C07D 301/32; C07D 303/23
(52) U.S. Cl. ................ 549/542; 549/541; 549/555; 549/556; 549/558; 549/559; 549/560
(58) Field of Search ................ 549/542, 541, 549/555, 556, 558, 559, 560

(56) References Cited

U.S. PATENT DOCUMENTS 6,180,696 B1 * 1/2001 Wong et al. ............... 523/457
6,211,389 B1 * 4/2001 Dimke ...................... 549/542

OTHER PUBLICATIONS

Humphrey et al., *Separation Process Technology*. McGraw–Hill, 1997, first edition, pp. 26–45.
Humphrey et al., *Separation Process Technology*. McGraw–Hill, 1997, first edition, pp. 45–59.
Peters et al., *Chemical Separations and Measurements: Theory and Practice of Analytical Chemistry*. Saunders Golden Series, 1974, first edition, pp. 477–478.
Peters et al., *Chemical Separations and Measurements: Theory and Practice of Analytical Chemistry*. Saunders Golden Series, 1974, first edition, pp. 480–481.

* cited by examiner

*Primary Examiner*—Ba K. Trinh
(74) *Attorney, Agent, or Firm*—Stephen E. Reiter; Foley & Lardner

(57) ABSTRACT

In accordance with the present invention, methods have been developed for the reduction of the chloride content of epoxy compound starting materials. Invention methods comprise fractionating an epoxy compound starting material into portions (e.g., fractions or cuts) having different chloride content relative to the epoxy compound starting material. Certain of these collected portions (i.e., the portions fractionated and collected after collection of the forecut and before discontinuation of the fractionation) contain substantially reduced chloride levels relative to the epoxy compound starting material.

20 Claims, 1 Drawing Sheet

METHODS OF REDUCING CHLORIDE CONTENT IN EPOXY COMPOUNDS

FIELD OF THE INVENTION

The present invention relates to the field of microelectronic devices, and more particularly to methods for reducing the chloride content of epoxy compound starting materials which are subsequently used to formulate encapsulants and underfills for microelectronic devices.

BACKGROUND OF THE INVENTION

Microelectronic devices are useful in a variety of consumer and industrial applications. Microelectronic devices are prepared utilizing a variety of chemical formulations, e.g., encapsulants and/or underfills. A typical component of encapsulants and underfills is a compound having at least one epoxy reactive group. A common impurity of such epoxy-containing compounds is chloride. Unfortunately, chloride is known to corrode the wire bonds within microelectronic devices. Thus, a major problem associated with microelectronic devices is the tendency of certain residual impurities (e.g., chloride) within the microelectronic devices to decrease the reliability of the device by promoting the corrosion of the wire bonds within the device, thereby increasing the risk of the device's failure.

There are only limited examples of the use of distillation to purify epoxy resins. Previously described distillation methods to purify epoxy resins suffer from several limitations. For example, known methods do not substantially reduce chloride content. In addition, known methods have only been described with respect to specifically defined diepoxides. Thus, there is no suggestion in the prior art that such methods are generally applicable to epoxides as a class.

Further, known methods require elevated temperatures. These elevated temperatures increase the risk of homopolymerization of the epoxy resin, which will lead to increased viscosity thereof, and reduced processibility of the encapsulant and/or underfill made therefrom. Moreover, these elevated temperatures increase the risk of side reactions of the epoxy resin, which will lead to decreased purity of the specifically defined diepoxide. Alternatively, prior art methods may require heat transfer and/or residence time which are insufficient to promote the requisite purification of the epoxy resin.

Accordingly, there remains a need in the art for new and better methods of reducing chloride content of epoxy compounds, particularly those used as starting materials in the formulation of electronic materials for the assembly of microelectronic devices. In addition, there is a need for epoxy compounds having reduced chloride content. Further, there is a need to ensure that these epoxy compounds do not suffer from increased viscosity.

SUMMARY OF THE INVENTION

In accordance with the present invention, there are provided methods for the reduction of the chloride content of epoxy compound starting materials. Invention methods comprise fractionating an epoxy compound starting material into portions (e.g., fractions or cuts) having different chloride content relative to the epoxy compound starting material. Certain of these collected portions (i.e., the portions fractionated and collected after collection of the forecut and before discontinuation of the fractionation) contain substantially reduced chloride levels relative to the epoxy compound starting material.

In an additional aspect of the present invention, there are provided reduced chloride content epoxy compounds produced by invention methods.

In a further aspect of the present invention, there are provided methods for producing a reduced viscosity formulation made from a treated epoxy compound, wherein the reduced viscosity formulation has a reduced viscosity relative to an analogous formulation made from an epoxy compound starting material. Invention methods comprise fractionating an epoxy compound starting material (e.g., an epoxy diluent, an epoxy resin, and the like) into portions (e.g., fractions or cuts) having different viscosities relative to the epoxy compound starting material. Surprisingly, formulations for encapsulants and/or underfills made from certain of these collected portions (i.e., the portions fractionated and collected after collection of the forecut and before discontinuation of the fractionation) exhibit substantially reduced viscosity levels relative to analogous formulations for encapsulants and/or underfills made from the epoxy compound starting material. Typically, the reduced viscosity formulations made from the collected portions also contain substantially reduced chloride levels relative to the corresponding formulations made from the epoxy compound starting material.

The present invention provides many advantages over the art. For example, invention methods and compounds are useful in preparing more reliable microelectronic devices. In addition, invention methods which reduce the viscosity of a formulation are useful in increasing the processibility of the formulation utilized in the preparation of microelectronic devices, thereby decreasing the cost of the prepared device and reducing the incidence of device failure. Other advantages of the present invention can be readily recognized by those of ordinary skill in the art.

DETAILED DESCRIPTION OF THE INVENTION

Figure 1:
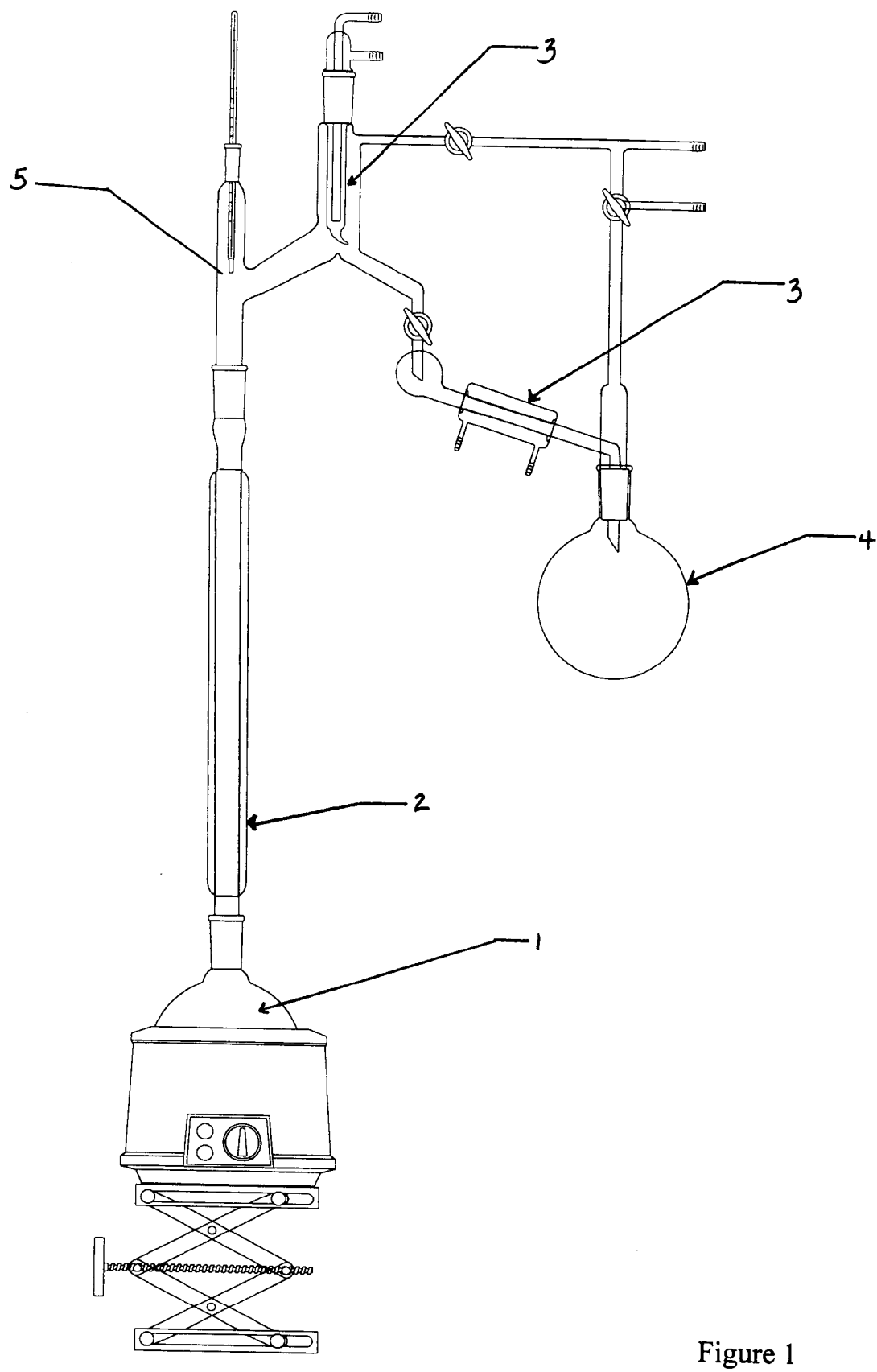
FIG. 1 is a schematic drawing of a fractional distillation apparatus useful in the practice of the present invention.

In accordance with the present invention, there are provided methods of reducing the chloride content of epoxy compound starting materials. Invention methods comprise fractionally distilling an epoxy compound having a first chloride content to form a plurality of fractions, and collecting the fractions having a chloride content less than the first chloride content, thereby producing an epoxy compound having a second (reduced) chloride content.

As utilized herein, "chloride" includes ionic chlorine, hydrolyzable chlorine (e.g., C—Cl containing compounds, 1,2 chlorohydrin, and the like), and non-hydrolyzable chlorine (e.g., methyl chloride and the like). Chloride content is the amount of chloride present in, or associated with, an epoxy-containing compound (e.g., an epoxy compound starting material, portions thereof, a treated epoxy compound, and the like). The chloride content can readily be determined in a variety of ways, as are well known to those of skill in the art. See, for example, ASTM D-18470 (for measuring amount of total chloride) and ASTM D-1726 (for measuring amount of hydrolyzable chlorides). Exemplary methods which can be employed for this purpose include X-ray fluorescence spectroscopy (XRF), infrared spectroscopy (IR), gas chromatography (GC), gas chromatography-mass spectroscopy (GCMS), mass spectroscopy (MS), atomic absorption (AA), inductively coupled plasma (ICP), and the like.

Epoxy compound starting materials contemplated for treatment in accordance with the present invention include epoxy resins and epoxy diluents. Epoxy resins include resins in liquid or solid form which have at least two epoxy groups and which are capable of cross linking (i.e., homo- or hetero-polymerizing) in a formulation useful as an encapsulant or an underfill for microelectronic devices. Epoxy resins may have a range of molecular weights, and specifically include low molecular weight epoxy resins, which are epoxy resins having a molecular weight of no greater than about 500. Epoxy resins can have a variety of epoxy equivalent weights (EEW), including EEWs in the range from about 45 to about 500, in a preferred range from about 90 to about 230, or in a presently preferred range from about 125 to about 200. Exemplary epoxy resins contemplated for use in the practice of the present invention include resins typically having in the range of about 2 to about 6 glycidyl groups, with a preferred range of about 2 to about 4 glycidyl groups. Exemplary epoxy resins include resins of the general formulae:

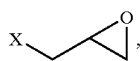

wherein X=

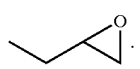

Additional exemplary epoxy resins include

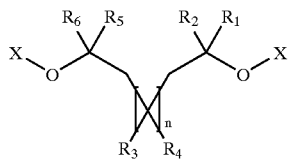

wherein:
X is as defined above,
each of $R_1$–$R_6$ is independently selected from hydrogen, a lower alkyl or a halogen, and
n=0 to 8; or

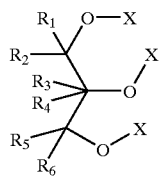

wherein X and $R_1$–$R_6$ are as defined above; or

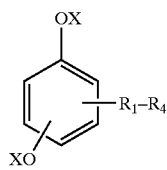

wherein X and $R_1$–$R_4$ are as defined above; or

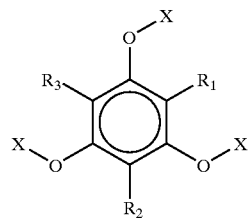

wherein X and $R_1$–$R_3$ are as defined above; or

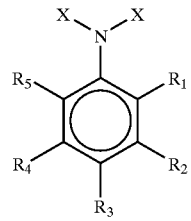

wherein X and $R_1$–$R_5$ are as defined above; or

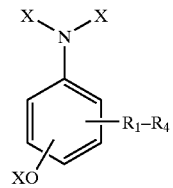

wherein X and $R_1$–$R_4$ are as defined above; or

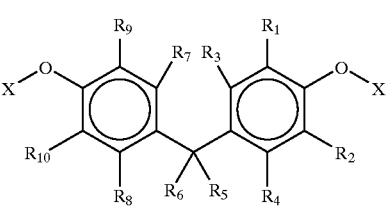

wherein X is as defined above and each of $R_1$–$R_{10}$ is independently selected from hydrogen, a lower alkyl or a halogen; or

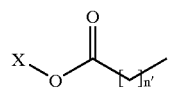

wherein X is as defined above and n'=1 to 16; or

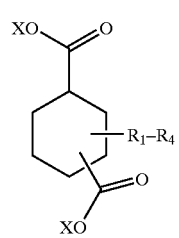

wherein X and $R_1$–$R_4$ are as defined above; or

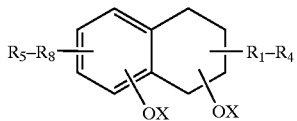

wherein X and $R_1$–$R_4$ and $R_5$–$R_8$ are as defined above, with the proviso that when both —OX groups are positioned on the same ring of the tetrahydrophthalate, the ring not having —OX groups acquires one of the $R_n$ groups of the ring having both —OX groups; or suitable combinations of any two or more thereof.

As used herein, "nonchloro-halogen" includes fluoride, bromide, or iodide radicals.

As used herein, "alkyl" includes acyclic, straight or branched chain radicals comprising a backbone having in the range of about 1 up to about 20 carbon atoms, wherein the carbon atoms of the backbone are linked by single bonds and have hydrogen radicals as their only other substituents, and one hydrogen radical is removed from the chain.

As used herein, "lower alkyl" refers to an alkyl wherein the backbone has in the range of about 1 to about 6 carbon atoms.

As used herein, "substituted alkyl" or "substituted lower alkyl" refers to an alkyl or lower alkyl, respectively, wherein one or more of the hydrogen radicals has been replaced by other substituent(s) such as radical(s) of hydroxy, alkoxy (of a lower alkyl), mercapto (of a lower alkyl), nonchloro-halogen, trifluoromethyl, cyano, nitro, amino, carboxyl, carbamate, sulfonyl, sulfonamide, and the like.

Specific examples of epoxy resins contemplated for use in the practice of the present invention include N,N-diglycidyl aniline, N,N-diglycidyl-4-glycidyloxyaniline, diglycidyl 1,2-cyclohexanedicarboxylate, diglycidyl 1,2,3,6-tetrahydrophthalate, bis(4-glycidyloxyphenyl)methane, 4,4'-isopropylidenediphenol diglycidyl ether, resorcinol diglycidyl ether, and the like, and suitable combinations of any two or more thereof.

Epoxy diluents contemplated for use in the practice of the present invention include liquid diluents which comprise at least one epoxy group and which have a viscosity which is sufficiently low to permit the liquid diluent to function as a viscosity reducer in a formulation useful as an encapsulant or underfill for microelectronic devices. Epoxy diluents include liquid diluents which are capable of cross linking (i.e., homo- or hetero-polymerizing) in a formulation useful as an underfill or an encapsulant for microelectronic devices. Epoxy diluents can have a variety of epoxy equivalent weights (EEW), including EEWs in the range from about 45 to about 250, in a preferred range from about 90 to about 250, or in a presently preferred range from about 100 to about 200. Exemplary epoxy diluents contemplated for use in the practice of the present invention include liquid diluents having in the range of about 1 to about 3 glycidyl groups, with a preferred range of about 1 to about 2 glycidyl groups. Exemplary epoxy diluents include liquid diluents of the general formnulae:

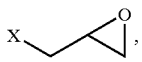

wherein Y=

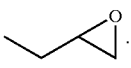

Additional exemplary diluents include

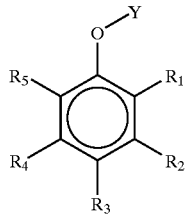

wherein:

Y is as defined above, and each of $R_1$–$R_5$ is independently selected from hydrogen, alkyl, substituted alkyl, or nonchloro-halogen; or

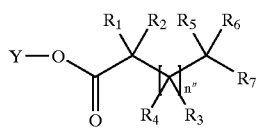

wherein:

Y is as defined above, each of $R_1$–$R_7$ is independently selected from hydrogen, alkyl, substituted alkyl, or nonchloro-halogen, and n" is 2 to 8; or

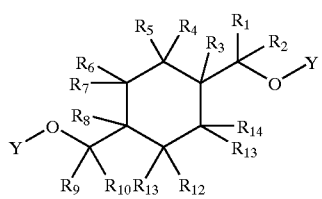

wherein:

Y is as defined above, and each of $R_1$–$R_{14}$ is independently selected from hydrogen, alkyl, substituted alkyl, or nonchloro-halogen; or

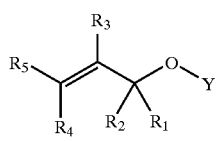

wherein:

Y is as defined above, and each of $R_1$–$R_5$ is independently selected from hydrogen, alkyl, substituted alkyl, or nonchloro-halogen; or

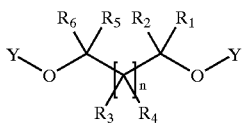

wherein:
Y is as defined above, and
each of $R_1$–$R_6$ is independently selected from hydrogen, alkyl, substituted alkyl, or nonchloro-halogen; and
n=0 to 6; or

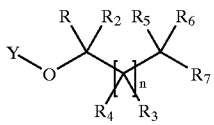

wherein:
Y is as defined above, and
each of $R_1$–$R_7$ is independently selected from hydrogen, alkyl, substituted alkyl, or nonchloro-halogen; and
n=0 to 8; or

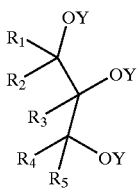

wherein:
Y is as defined above, and
each of $R_1$–$R_5$ is independently selected from hydrogen, alkyl, substituted alkyl, or nonchloro-halogen; or

wherein:
Y is as defined above, and
R is selected from hydrogen, alkyl, substituted alkyl, or nonchloro-halogen; or suitable combinations of any two or more thereof.

Specific examples of epoxy diluents contemplated for use in the practice of the present invention include 1,4-butanediol diglycidyl ether; neopentyl glycol diglycidyl ether; 1,2-epoxy-3-phenoxypropane; benzyl glycidyl ether; glycidyl isopropyl ether; glycidyl isobutyl ether; glycidyl methyl ether; glycidyl 2-methylphenyl ether; glycidyl 4-methoxyphenyl ether; glycidyl 4-nonylphenyl ether; 1,4-cyclohexanedimethanol diglycidyl ether; 4-tert-butylphenyl glycidyl ether; butyl glycidyl ether; tert-butyl glycidyl ether; trimethylolpropane triglycidyl ether; allyl glycidyl ether; and the like; and suitable combinations of any two or more thereof.

As utilized herein, the term "fractionating" refers to any means for separating an epoxy compound starting material having an initial chloride content into various portions (e.g., fractions or cuts), where each portion has a chloride content different from the initial chloride content. Fractionating (i.e., separating) can readily be accomplished in a variety of ways, as are well known to those of skill in the art. Typically, fractionating is accomplished by applying reduced pressure and/or heat (i.e., increasing temperature) to the epoxy compound starting material in an apparatus designed to fractionate the various components of the epoxy compound starting material (e.g., fractional vacuum distillation apparatus, and the like).

Optionally, the average chloride content of the collected fractions may be reduced by a predetermined percentage relative to the chloride content of the epoxy compound starting material. As utilized herein, the term "average chloride content" means the mean of the chloride contents of the collected fractions.

The reduction in the average chloride content can vary over a wide range, expressed herein as an average chloride reduction range. Typically, the low end point of this average chloride reduction range is greater than or equal to about 50%. Another way to express acceptable values for the low end point of this average chloride reduction range is as any integer percentage value in the range from about 50% to less than about 99%. Exemplary low end points of this average chloride reduction range include 50%, 70%, 90%, 95%, and 98%. The corresponding upper end point of this average chloride reduction range is less than or equal to about 99%. Another way to express acceptable values for this corresponding upper end point of the average chloride reduction range is as any integer percentage value greater than the selected low end point of this range and in the range from greater than about 50% to about 99%. Exemplary high endpoints of this average chloride reduction range include 51%, 70%, 95% and 99%.

Frequently, the desired collected fractions (i.e., the collected fraction(s) having reduced chloride content, the second cut, and the like) have an average viscosity which is less than the viscosity of the epoxy compound starting material. The magnitude of this decrease in viscosity can be expressed in a variety of ways, e.g., in percentage terms, in absolute terms, and the like. When expressed in percentage terms, the viscosity reduction of the collected fractions is greater than or equal to about 5%, and less than or equal to about 35%. When expressed as an absolute value, the viscosity reduction of the collected fractions can be defined as a viscosity reduction by at least about 2 centipoise (cps), up to about 500 cps.

Fractionation contemplated in the practice of the present invention can be carried out in a variety of ways, e.g., by fractional vacuum distillation, and the like. Fractional vacuum distillation can be carried out utilizing a fractionator, which is an apparatus capable of performing fractional vacuum distillation or, more generally, capable of subjecting the epoxy compound starting material to reduced pressures and/or increased temperatures sufficient to fractionate an epoxy compound starting material.

Typically, the fractionating (e.g., via fractional vacuum distillation, and the like) can be carried out at a reduced pressure of no greater than about 10 torr. Optionally, the reduced pressure can be as low as about 0.015 torr. Generally, the lower the pressure, the lower the temperature needed to perform a particular fractionation, and the lower the risk of polymerizing or increasing the viscosity of the epoxy compound starting material. The reduced pressure in the fractionator can be achieved in a variety of ways (e.g., vacuum pump, and the like), as known to those of skill in the art.

For example, the reduced pressure can vary over a wide range, expressed herein as a reduced pressure range. The low end point of this reduced pressure range is typically any value which is an integer multiple of 0.01 torr and which is in the range from about 0.015 torr up to about 2 torr.

Exemplary low end points of this reduced pressure range include 0.015 torr, 0.050 torr, 0.1 torr, 0.2 torr, 0.3 torr, 0.4 torr, 0.5 torr, 0.75 torr, 1 torr, 1.5 torr, and 2 torr. The corresponding high point of this reduced pressure range is commonly any value which is an integer multiple of about 0.01 torr, and which is greater than the selected low end point of this range, and which is in the range from about 0.05 torr up to about 10 torr. Exemplary upper end points for the reduced pressure ranges include 0.05 torr, 0.10 torr, 0.15 torr, 0.16 torr, 0.17 torr, 0.18 torr, 0.19 torr, 0.20 torr, 0.25 torr, 0.30 torr, 0.40 torr, 0.50 torr, 0.60 torr, 0.70 torr, 0.80 torr, 0.90 torr, 1.0 torr, 1.5 torr, 2.0 torr, 5.0 torr and 10.0 torr.

The reduced pressure employed in the practice of the present invention can be varied depending on the type and/or amount of epoxy compound starting material being fractionated, the concentration of the chloride impurity, the presence of other components in the epoxy compound starting material being treated, the number of theoretical plates in the fractionator, the desired yield of treated epoxy compound, and the like. Thus, for example, when the epoxy compound starting material is an epoxy diluent, the preferred pressure range is from about 0.1 torr up to about 1 torr. Similarly, when the epoxy compound starting material is a low molecular weight epoxy resin, the preferred pressure range is from about 0.015 torr up to about 0.2 torr.

In addition, the fractionating (e.g., via fractional vacuum distillation, and the like) can frequently be carried out at an elevated temperature which can vary over a wide range, expressed herein as a fractionating temperature range. Typically, the low end point of this fractionating temperature range is greater than or equal to about 50° C. Another way to express acceptable values for the low end point of this fractionating temperature range is as any integer temperature value in the range from about 50° C. to about 150° C. Exemplary low end points of this fractionating temperature range include 50° C., 80° C., 95° C., 105° C., 120° C., and 150° C. The corresponding upper end point of this fractionating temperature range is commonly less than or equal to about 160° C., and is generally kept below the temperature wherein substantial polymerization can occur with respect to the epoxy compound starting material whose temperature is being elevated. Another way to express acceptable values for the upper end point of this fractionating temperature range is as any integer temperature value which is greater than the selected low end point of the range and which is in the range from about 95° C. to about 160° C. Exemplary upper end points of this fractionating temperature range include 95° C., 100° C., 105° C., 110° C., 115° C., 120° C., 125° C. 150° C., and 160° C.

Further, the residence time of the epoxy compound starting material, i.e., the time during which heat and/or reduced pressure is being applied to the epoxy compound starting material in accordance with the invention, can vary significantly. The residence time may be within the range having as a low end point any value from about ⅓ hour to about 1 hour, and as an upper end point any value greater than the low end point and from about 1 hour to about 100 hours. Exemplary ranges for residence times include a range of about 4 hours to about 60 hours, a preferred range of about 6 hours to about 60 hours, and a presently preferred range of about 8 hours to about 40 hours.

Typically, the fractionator utilized to perform the fractional vacuum distillation comprises at least one column, such as a Vigreux column, a random packed column, a tray column, a spinning band column, a plain column, and the like. These and other columns contemplated for use in the fractionator employed in the practice of the present invention are generally well known to those of skill in the art. See, for example, Peters, D. G., et al., *Chemical Separations and Measurements*, pp.480–481 (W.B. Saunders Company (Pub), 1$^{st}$ Ed., 1974); Humphery, J. L., et al., *Separation Process Technology*, pp. 45–59 (McGraw-Hill, 1$^{st}$ Ed., 1997).

As utilized herein, the term "random packed column" includes columns packed with one or more column packing materials, e.g., Pro-Pack™, glass beads, Rasching rings, Intalox Saddles™, Berl Saddles, Pall™ Rings, Cascade™ Mini Rings, and the like, and suitable combinations of any two or more thereof.

As utilized herein, "tray column" includes sieve tray columns, valve tray columns, bubble-cap columns, Nye™ tray columns, Max-Frac™ tray columns, Screen™ tray columns, Ultra-Frac™ tray columns, Trutna tray columns, Oldershaw columns, and the like.

As utilized herein, "plain (hemple) column" refers to a straight sided, uninsulated column with dimples at the bottom for supporting column packings, wherein the use of column packings is optional.

Fractionators employed in the practice of the present invention can be made from a wide variety of materials which do not substantially react with the epoxy compound starting material or constituents thereof, e.g., plastic, glass, ceramic, various metals, and the like.

Fractionators (and components thereof) may optionally be insulated and/or heated and/or treated and/or modified in a manner which increases the efficiency of the fractionation. As utilized herein, "efficiency of the fractionation" means the percentage yield of end product having a reduced chloride content (relative to the chloride content of the epoxy compound starting material). The efficiency of the fractionation can be modulated by varying boilup (i.e., slow boil up provides for greater efficiency), varying the reflux ratio (i.e., greater reflux ratio provides for greater efficiency of the fractionation), varying the length of the column (i.e., taller/longer columns provide for greater efficiency of fractionation), varying the column packing material, and the like, and suitable combinations of two or more thereof. As known to those of skill in the art, the efficiency of the fractionation is a function of the desired yield and the desired purity of, and the desired throughput for production of, the treated epoxy compound, and other like variables.

Fractionators employed in the practice of the present invention typically have at least two theoretical plates. As readily recognized by those of skill in the art, it may be desirable to vary the number of theoretical plates present in the fractionator, depending on the epoxy compound starting material being fractionated, the concentration of the chloride impurity, and the presence of other components in the epoxy compound starting material being treated. The number of theoretical plates of a particular fractionator can be calculated utilizing methodology generally well known to those of skill in the art. See, for example, Peters, D. G., et al., *Chemical Separations and Measurements*, pp.477–478 (W.B. Saunders Company (Pub), 1$^{st}$ Ed., 1974); Humphery, J. L., et al., *Separation Process Technology*, pp. 26–45 (McGraw-Hill, 1$^{st}$ Ed., 1997).

The number of theoretical plates suitable for use in the practice of the present invention can vary over a wide theoretical plate value range. Typically, the low end point of this theoretical plate value range is at least about 2. Another way of expressing acceptable values for the low end point of this theoretical plate value range is as any integer value in the range from about 2 to less than about 30. Exemplary low end points of this theoretical plate value range include 2, 3, 6, 10, 15, 20, 25, and 29. The corresponding upper end point of this theoretical plate value range is frequently less than or equal to about 30. Another way of expressing acceptable values for this corresponding upper end point of the average chloride reduction range is as any integer value greater than the selected low end point of this range and in the range from greater than about 2 to about 30. Exemplary upper end points of this theoretical plate value range include 3, 6, 10, 15, 20, 25, and 30.

In accordance with another embodiment of the present invention, there are provided methods of treating epoxy compound starting materials to produce products having a chloride content less than a predetermined reduced chloride value, relative to the chloride content of the epoxy compound starting material. Invention methods comprise fractionating the epoxy compound starting material to form a plurality of cuts, and collecting a first cut having a chloride content greater than a predetermined reduced chloride value, and collecting a second cut having a chloride content less than or equal to the predetermined reduced chloride value.

The predetermined reduced chloride value can be expressed in a variety of ways. For exarnple, the predetermined reduced chloride value can be expressed as a relative value, an absolute value, and the like.

As a relative value, the predetermined reduced chloride value is generally a percentage value (i.e., less than 100%) of the chloride content of the epoxy compound starting material, and is selected from a range of such values. Typically, the low end point of the predetermined reduced chloride value range is greater than or equal to about 1%. Another way of expressing acceptable values for the low end point of this predetermined reduced chloride value range is as any integer percentage value in the range from about 1% to about 60%. Exemplary low end points of this predetermined reduced chloride value range include 1%, 5%, 10%, 30%, 50%, and 60%. The corresponding upper end point of this predetermined reduced chloride value range is commonly less than or equal to about 75%. Another way of expressing acceptable values for this corresponding upper end point of this predetermined reduced chloride value range is as any integer percentage value which is greater than the low end point of this predetermined reduced chloride value range and which is in the range from about 10% to about 75%. Exemplary upper end points of this predetermined reduced chloride value range include 10%, 15%, 20%, 30%, 50%, and 75%. When selected from such specifically defined ranges, exemplary relative values for the predetermined reduced chloride value include 75%, 50%, 30%, 10%, 5% and 1% of the chloride content of the epoxy compound starting material.

Alternatively, the predetermined reduced chloride value relative to the chloride content of the epoxy compound starting material can be expressed as an absolute value. Thus, the predetermined reduced chloride value can be a specific reduction in the chloride content of the second cut, relative to the chloride content of the epoxy compound starting material. This specific reduction can be defined as a chloride reduction so that the predetermined reduced chloride value does not exceed a value in the range from about 100 to about 5,000 ppm, with a value in the range from about 200 ppm to about 1000 ppm being presently preferred.

As readily recognized by those of skill in the art, the predetermined reduced chloride value, relative to the chloride content of the epoxy compound starting material, may vary depending on a variety of factors. These factors include initial chloride content of the epoxy compound starting material, desired chloride reduction in the treated epoxy compound, the boiling point of the epoxy compound starting material, the number of glycidyl groups of the epoxy compound starting material, the molecular weight of the epoxy compound starting material, the presence of other organic functionality(ies) on the epoxy compound starting material, the desired yield of treated epoxy compound, and the like.

Optional steps and/or parameters contemplated for incorporation into invention methods can further increase the efficiency of the invention methods. For example, the first portion (e.g., first cut or first fraction) and/or any epoxy compound starting material remaining after collection of the second portion (e.g., second cut or second fraction) can optionally be recycled.

Optionally, the first portion (e.g., first cut or first fraction) and/or any epoxy compound starting material remaining after collection of the second portion (e.g., second cut or second fraction) can be discarded.

The first cut and/or the second cut can be obtained by any known means of collection. For example, the first cut can be obtained by applying heat to the epoxy compound starting material (under reduced pressure) until at least some distillate has been collected, and until the overhead temperature has remained constant or nearly constant at a substantially constant pressure for a time time sufficient to determine that a substantial amount of said first cut has been collected, and the second cut can be obtained by continuing to apply heat (under reduced pressure) to the epoxy compound starting material remaining after collection of the first cut until additional distillate has been collected, and until the overhead temperature (at a substantially constant pressure) has increased by no greater than about 10° C. since termination of collection of the first cut.

As utilized herein, "apply(ing) heat" means increasing the temperature of the epoxy compound starting material in the fractionator by any means known in the art (e.g., gas burner, electric heater, and the like). Exemplary increased temperatures of the epoxy compound starting material are as set forth above. Frequently, heat can be applied slowly to avoid certain problems associated with fractionating certain epoxy compound starting materials, e.g., flashing, bumping, and the like.

As utilized herein, "overhead temperature" means the temperature in the fractionating apparatus utilized for fractionating the epoxy compound starting material (e.g., a fractionator when the fractionating means is fractional vacuum distillation), as measured immediately prior to condensation of the vaporized epoxy compound starting material, which condensation initiates the collecting step. Thus, as shown for example in FIG. 1, when the fractionating means is fractional vacuum distillation utilizing a fractionator comprising a vaporization flask (1), a column (2), a condenser (3), and a collection flask (4), the overhead temperature is that temperature measured at the top (5) of the column (see FIG. 1).

In a further aspect of the invention methods, the first cut can be obtained by applying heat to the epoxy compound starting material (under reduced pressure) until at least about 10 vol/vol % to about 15 vol/vol % of the epoxy compound starting material has been collected, and the second cut can be obtained by continuing to apply heat (under reduced pressure) to the epoxy compound material remaining after collection of the first cut, until at least about 50 vol/vol % to about 70 vol/vol % of the epoxy compound starting material has been collected. Alternatively, the second cut can be obtained as a plurality of additional cuts collected until at least about 50 vol/vol % to about 70 vol/vol % of the epoxy compound starting material has been collected as additional cuts. In accordance with this aspect of the present invention, each additional cut is collected by applying heat (under reduced pressure) to the epoxy compound starting material remaining upon the later of the conclusion of the collection of the first cut and the conclusion of the collection of the previous cut until at least about 1 vol/vol % to about 5 vol/vol % of the epoxy compound starting material has been collected.

In accordance with another aspect of the invention, the decision of when to collect the first cut and/or the second cut can be guided by live analytical feedback methodology known in the art, which methodology is capable of measuring the chloride content of an epoxy compound starting material. Thus, the first cut can be obtained by applying heat (under reduced pressure) to the epoxy compound starting material until at least some distillate has been collected, and until a marginal chloride content of the distillate is no greater than a predetermined marginal reduced chloride value, and the second cut may be obtained by continuing to apply heat (under reduced pressure) to the epoxy compound starting material remaining upon the conclusion of the collection of the first cut until additional distillate has been collected, and until the marginal chloride content of the additional distillate is greater than the predetermined marginal reduced chloride value. The predetermined marginal reduced chloride value is generally determined as a reduced chloride content relative to the chloride content of the epoxy compound starting material.

As utilized herein, "marginal chloride content" means the chloride content of a sample of the most recently collected distillate, which chloride content is measured between the place/time in the fractionating apparatus where the overhead temperature of the sample is measured and the place/time where the sample is integrated into the larger collected distillate.

The predetermined marginal reduced chloride value can vary significantly over a wide range, expressed herein as a marginal reduced chloride range. Typically, the low end point of this marginal reduced chloride range is less than or equal to 50% of the chloride content of the epoxy compound starting material. Another way of expressing acceptable values for the low end point of this marginal reduced chloride range is as any integer percentage value in the range from about 1% to about 50% of the chloride content of the epoxy compound starting material. Exemplary low end points of this marginal reduced chloride range include 1%, 5%, 10%, 30%, 35%, and 49% of the chloride content of the epoxy compound starting material. The corresponding upper end point of this marginal reduced chloride range is generally greater than 10% of the chloride content of the epoxy compound starting material. Another way of expressing acceptable values for this upper end point of the marginal reduced chloride range is as any integer percentage value in the range from about 10% to about 75% of the chloride content of the epoxy compound starting material. Exemplary upper end points of this marginal reduced chloride range include 10%, 30%, 50%, and 75% of the chloride content of the epoxy compound starting material. This predetermined marginal reduced chloride value may be varied depending upon the end use contemplated for the epoxy resin starting material having reduced chloride content.

In an additional aspect of the present invention, there are provided reduced chloride content epoxy compounds made by any of the foregoing methods.

In a further aspect of the present invention, there are provided products prepared, utilizing reduced chloride content epoxy compounds made in accordance with any of the foregoing methods. These products include formulations for encapsulants and underfills utilized in the preparation of microelectronic devices, and the like. As utilized herein, "formulation" means any combination of epoxy resin(s), epoxy diluent(s), epoxy hardeners and/or catalysts (preferably nitrogen based catalysts, e.g., amines), and/or fillers (e.g., silica, hydrated alumina calcium carbonate, and the like), which combination is utilized to encapsulate electronic devices or underfill flip chips. Optionally, formulations include adhesion promoters, pigments and/or fill agents, and the like.

In an additional aspect of the present invention, there are provided methods to make a reduced viscosity formulation employing a treated epoxy compound, which reduced viscosity formulation has a reduced viscosity relative to an analogous formulation made from an epoxy compound starting material. Invention methods comprise fractionating an epoxy compound starting material into portions (e.g., fractions or cuts) having different viscosities relative to the epoxy compound starting material, and collecting the portions having a lower viscosity than the epoxy compound starting material to form the treated epoxy compound, and adding sufficient necessary formulation components to the treated epoxy compound to produce the formulation.

The viscosity of the portions and of the epoxy compound starting material can be measured through the use of apparatus and methodology(ies) well known to those of skill in the art, for example, concentric cylinder viscometer (e.g., Brookfield viscometer and the like), cone and plate viscometer, controlled stress rheometer, and the like.

In a further aspect of the present invention, there are provided reduced viscosity formulations made according to the foregoing methods. Frequently, these reduced viscosity formulations have a reduced chloride content relative to the analogous formulation made from the epoxy compound starting material.

All percentages provided herein, comparing the amount of treated epoxy compound to the amount of the epoxy compound starting material, are volume/volume percentages. However, as recognized by those of skill in the art, the density between the epoxy compound starting materials and the treated epoxy compounds remain nearly constant during the treatment process, thereby permitting interchangeability of volume/volume percentages and weight/weight percentages.

All references cited herein are hereby incorporated herein by reference.

The invention will now be described in greater detail with reference to the following non-limiting examples.

EXAMPLE 1

Fractional Distillation of 4-tert-Butylphenyl Glycidyl Ether

An initial sample of 800 g of 4-tert-butylphenyl glycidyl ether (commercially available as HELOXY Modifier 64 from Shell Chemical Company of Houston, Tex., containing greater than 2000 ppm chloride) was subjected to fractional vacuum distillation utilizing a 20 cm vacuum jacketed Vigreux distillation head (commercially available as CG-1246-12 from Chemglass, Inc. of Vineland, N.J.). Four fractions (i.e. cuts) of the initial sample were collected at varying temperatures and pressures. The epoxy equivalent weight (EEW), together with the yield (calculated as a weight % of the initial sample) of each of the fractions was calculated. In addition the chloride content of the initial sample, each of the four fractions and the remaining amount of the initial sample after collection of each of the four fractions (i.e., the pot) were measured using X-ray fluorescence spectroscopy (XRF). The results are shown in Table 1.

TABLE 1

| Sample # | Temp (° C.) | Pressure (mm Hg) | EEW | Yield % | Chloride Content (PPM) |
|---|---|---|---|---|---|
| Initial Material | N/A | N/A | 235 | N/A | 2033 |
| 1 | 25–105 | 0.07–0.08 | 205 | 19.4 | 707 |
| 2 | 105–115 | 0.06–0.08 | 205 | 24.6 | 644 |
| 3 | 95–105 | 0.095–0.11 | 204 | 24.1 | 607 |
| 4 | 97–101 | 0.05 | 207 | 26.3 | 834 |
| Pot | N/A | N/A | | 5.7% | |

After distillation, there was a combined usable material of 755 g (94.4% yield) of 4-tert-butylphenyl glycidyl ether (i.e. Heloxy 64) which had a chloride content of less than 850 ppm, which represents an approximately 60% reduction in chloride content relative to the starting material.

EXAMPLE 2

Fractional Distillation of Diglycidyl Ether of 1,4-Butanediol

An initial sample of 900 g of diglycidyl ether of 1,4-butanediol (commercially available as Araldite DY O26 from Ciba Specialty Chemicals of Hawthorne N.Y., containing greater than 3000 ppm chloride) was subjected to fractional vacuum distillation utilizing a variable reflux distillation head and a 30 cm vacuum jacketed distillation column, which was ¾ full of Pro-Pack™. Three fractions (i.e. cuts) of the initial sample were collected at varying temperatures and pressures. The epoxy equivalent weight (EEW), together with the yield (calculated as a weight % of the initial sample) of each of the fractions was calculated. In addition the chloride content of the initial sample, each of the three fractions and the remaining amount of the initial sample after collection of each of the three fractions (i.e., the pot) were measured using XRF. The results are shown in Table 2.

TABLE 2

| Sample # | Temp (° C.) | Pressure (mm Hg) | EEW | Yield % | Chloride Content (PPM) |
|---|---|---|---|---|---|
| Initial Material | N/A | N/A | 112 | N/A | 3115 |
| 1 | 25–91 | 0.15 | 124 | 24560 | |
| 2 | 91–98 | 0.15 | 102 | 35 | 220 |
| 3 | 98–105 | 0.12 | 102 | 32 | 186 |
| Pot | 191 | N/A | 107 | 22 | 6238 |

After distillation, there was a combined usable material of 603 g (67% yield) of the diglycidyl ether of 1,4-butanediol ether (i.e. Araldite DYO26) which had a chloride content of less than 250 ppm, which represents a dramatic 90% reduction in chloride content relative to the starting material.

EXAMPLE 3

Fractional Distillation of Neopentyl Glycol Diglycidyl Ether (Predistillation Performed)

An initial 4115 g sample of neopentyl glycol diglycidyl ether (commercially available as HELOXY Modifer 68 from Shell Chemical Company of Houston, Tex., containing greater than 35,000 ppm chloride) was predistilled using a short path distillation head from 23–125° C. at 0.08–0.10 torr for 8 hours. Upon discontinuation of the predistillation, 3144 g of predistillate had been collected. The predistillate was subjected to fractional vacuum distillation utilizing a variable reflux distillation head and a 30 cm vacuum jacketed distillation column, which was ⅔ full of Pro-Pack™. Eighteen fractions (i.e. cuts) of the initial sample were collected at varying temperatures and pressures. The epoxy equivalent weight (EEW), together with the yield (calculated as a weight % of the initial sample), of each of the fractions was calculated. In addition the chloride content of the initial sample, each of the eighteen fractions and the remaining amount of the initial sample after collection of each of the eighteen fractions (i.e., the pot) were measured using XRF. The results are shown in Table 3.

TABLE 3

| Sample # | Temp (° C.) | Pressure (mm Hg) | EEW | Yield %[1] | Grams | Chloride Content (PPM) |
|---|---|---|---|---|---|---|
| Initial Material | N/A | N/A | 193 | 100 | 4115 | 35185 |
| Predistillate | 25–135 | 0.08–0.1 | 126 | 76.4 | 3143.7 | 13520 |
| 1 | 57.0–64.0 | 0.27–0.5 | 163.9 | 1.4 | 56.2 | 7883 |
| 2 | 54.0–60.0 | 0.22–0.38 | 153.9 | 2.1 | 86.62 | 7546 |
| 3 | 53.5–61.0 | 0.2–0.28 | 160.4 | 1.7 | 71.1 | 7651 |
| 4 | 53.5–74.0 | 0.24–0.5 | 109.5 | 1.5 | 61.16 | 1852 |
| 5 | 74.0–76.5 | 0.22–0.24 | 108.3 | 6.2 | 253.7 | 329 |
| 6 | 76.0–76.5 | 0.20–0.24 | 107.7 | 6.6 | 271.5 | 227 |
| 7 | 75.0–79.0 | 0.21–0.48 | 107.5 | 4.0 | 163.9 | 253 |
| 8 | 76.5–77.5 | 0.23–0.28 | 108.3 | 1.6 | 67.3 | 304 |
| 9 | 75.0–75.5 | 0.21–0.38 | 107.8 | 5.2 | 212.4 | 204 |
| 10 | 75.0–75.5 | 0.21–0.24 | 107.6 | 4.9 | 202.5 | 206 |
| 11 | 75.5 | 0.23–0.24 | 107.8 | 6.6 | 272.2 | 180 |
| 12 | 75.5–76.0 | 0.22–0.23 | 108.3 | 6.6 | 272.6 | 250 |
| 13 | 75.0–75.5 | 0.22–0.24 | 107.5 | 2.1 | 87.7 | 171 |
| 14 | 73.5–75.5 | 0.20–0.23 | 108.0 | 6.3 | 260.1 | 298 |
| 15 | 75.5–76.5 | 0.23–0.24 | 107.7 | 4.1 | 167.5 | 257 |
| 16 | 75.5–77.0 | 0.25–0.25 | 108.0 | 1.0 | 39.8 | 265 |
| 17 | 76.0–78.0 | 0.25–0.28 | 108.7 | 1.2 | 50.9 | 290 |
| 18 | 78.0–82.0 | 0.25–0.29 | 111.0 | 0.4 | 15.4 | 566 |
| Pot | | | 190.7 | 11.9 | 489.1 | 74199 |

[1]All yields reported are based by weight on the initial 4115 g sample.

After distillation, there was a combined usable material of 2322 g (56.4% yield) of the diglycidyl ether of neopentyl glycol diglycidyl ether (i.e. HELOXY Modifer 68) which had a cholride content of less than 400 ppm. This represents a dramatic 90% decrease in chloride content relative to the starting material.

While the invention has been described in detail with reference to certain preferred embodiments thereof, it will be understood that modifications and variations are within the spirit and scope of that which is described and claimed.

What is claimed is:

1. A method of reducing the chloride content of an epoxy compound having a first chloride content to form an epoxy compound having a second chloride content less than the first chloride content, said method comprising:
 a) fractionally distilling said epoxy compound having a first chloride content to form a plurality of fractions; and
 b) collecting the fractions having a chloride content less than the first chloride content, thereby producing an epoxy compound having a second chloride content.

2. A method according to claim 1, wherein the average chloride content of said collected fractions is at least 50% less than said first chloride content.

3. A method according to claim 1, wherein said fractional distilling is accomplished by factional vacuum distillation.

4. A method according to claim 3, wherein said fractional vacuum distillation is carried out at a reduced pressure in the range of about 0.015 torr up to about 10 torr.

5. A method according to claim 3, wherein said fractional vacuum distillation is carried out utilizing a fractionator comprising a column selected from the group consisting of a Vigreux column, a random packed column, a tray column, a spinning band column, and a plain column.

6. A method according to claim 5, wherein said fractionator has about 2 to about 30 theoretical plates.

7. A method of treating an epoxy compound starting material to produce a product having a chloride content less than a predetermined reduced chloride value, relative to the chloride content of said epoxy compound starting material, said method comprising:

a) fractionating said epoxy compound starting material to form a plurality of cuts; and b) collecting a first cut having a chloride content greater than the predetermined reduced chloride value; and c) collecting a second cut having a chloride content no greater than the predetermined reduced chloride value.

8. A method according to claim 7, wherein the predetermined reduced chloride value relative to the chloride content of said epoxy compound starting material is 75% of the chloride content of said epoxy compound starting material.

9. A method according to claim 7, wherein the predetermined reduced chloride value relative to the chloride content of said epoxy compound starting material is 50% of the chloride content of said epoxy compound starting material.

10. A method according to claim 7, wherein said first cut is recycled.

11. A method according to claim 7, wherein any epoxy compound starting material remaining after step c) is recycled.

12. A method according to claim 7, wherein:

said first cut is obtained by applying heat to said epoxy compound starting material (under reduced pressure) until at least some distillate has been collected, and until the overhead temperature has remained nearly constant at a substantially constant pressure for a time sufficient to determine that a substantial amount of said first cut has been collected; and said second cut is obtained by continuing to apply heat (under reduced pressure) to said epoxy compound starting material remaining upon the conclusion of step b) until additional distillate has been collected, and until the overhead temperature has increased at a substantially constant pressure by about 10° C. since the conclusion of step b).

13. A method according to claim 7, wherein:

said first cut is obtained by applying heat to said epoxy compound starting material (under reduced pressure) until at least about 10% to about 15% of said epoxy compound starting material has been collected; and said second cut is obtained by continuing to apply heat (under reduced pressure) to said epoxy compound starting material remaining upon the conclusion of step b) until at least about 50% to about 70% of said epoxy compound starting material has been collected.

14. A method according to claim 13, wherein said second cut is obtained as a plurality of additional cuts collected until at least about 50% to about 70% of said epoxy compound starting material has been collected as additional cuts, wherein each additional cut is collected by slowly applying heat (under reduced pressure) to said epoxy compound starting material remaining upon the later of the conclusion of step b) and the conclusion of the collection of the previous additional cut until at least about 1% to about 5% of said epoxy compound starting material has been collected.

15. A method according to claim 7, wherein:

said first cut is obtained by applying heat to said epoxy compound starting material (under reduced pressure) until at least some distillate has been collected, and until the marginal chloride content of said distillate is no greater than a predetermined marginal reduced chloride value relative to the chloride content of said epoxy compound starting material; and said second cut is obtained by continuing to apply heat (under reduced pressure) to said epoxy compound starting material remaining upon the conclusion of step b) until additional distillate has been collected, and until the marginal chloride content of said additional distillate is greater than the predetermined marginal reduced value.

16. A method according to claim 15, wherein the predetermined marginal reduced chloride value is 50% of the chloride content of said epoxy compound starting material.

17. A reduced chloride content epoxy composition made according to the method of claim 1.

18. A method to make a reduced viscosity formulation employing a treated epoxy compound, which reduced viscosity formulation has a reduced viscosity relative to an analogous formulation made from an epoxy compound starting material, said method comprising:

a) fractionating an epoxy compound starting material into a plurality of portions having different viscosities relative to the epoxy compound starting material, b) collecting the portions having a lower viscosity than the epoxy compound starting material to form a treated epoxy compound, and c) adding sufficient necessary formulation components to said treated epoxy compound to form said formulation.

19. A reduced viscosity formulation made according to the method of claim 18.

20. A reduced viscosity formulation according to claim 19, wherein the reduced viscosity formulation has a reduced chloride content relative to the analogous formulation made from an epoxy compound starting material.

* * * * *

UNITED STATES PATENT AND TRADEMARK OFFICE
CERTIFICATE OF CORRECTION

PATENT NO. : 6,677,468 B1  Page 1 of 1
DATED : January 13, 2004
INVENTOR(S) : Dimke et al.

It is certified that error appears in the above-identified patent and that said Letters Patent is hereby corrected as shown below:

<u>Column 6,</u>
Lines 40-48, delete the structure and replace with the following, the second occurrence of "R13" in the sturcture should read -- R11 --:
--                                                                   --.

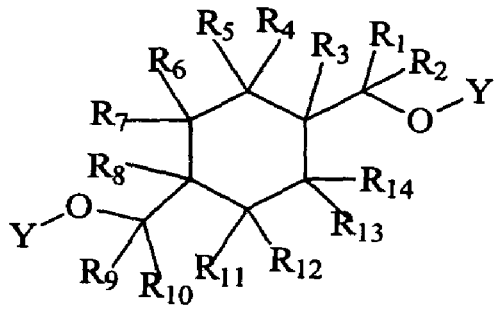

Line 48, after "125° C.," insert -- 140° C., --.

<u>Column 15,</u>
Line 50, Table 2, under the heading "Yield %" replace "24560" with -- 11 --; and under the heading "Chloride Content (PPM)," insert -- 24560 --.

Signed and Sealed this

Ninth Day of May, 2006

JON W. DUDAS
*Director of the United States Patent and Trademark Office*